US012765796B2

(12) United States Patent
Greiser et al.

(10) Patent No.: US 12,765,796 B2
(45) Date of Patent: Oct. 20, 2026

(54) LOCAL COIL AND MAGNETIC RESONANCE DEVICE

(71) Applicant: Siemens Healthineers AG, Forchheim (DE)

(72) Inventors: Andreas Greiser, Erlangen (DE); Miriam Keil, Erlangen (DE); Jens Thöne, Lauf an der Pegnitz (DE); Hans Weber, Erlangen (DE); Sebastian Dennert, Lonnerstadt (DE); Titus Lanz, Würzburg (DE); Florian Odoj, Veitshöchheim (DE); Marco Geißner, Estenfeld (DE); Manuel Graf, Estenfeld (DE); Marion Hellinger, Uttenreuth (DE); Jörg Rothard, Litzendorf (DE)

(73) Assignee: Siemens Healthineers AG, Forchheim (DE)

( * ) Notice: Subject to any disclaimer, the term of this patent is extended or adjusted under 35 U.S.C. 154(b) by 147 days.

(21) Appl. No.: 18/647,441

(22) Filed: Apr. 26, 2024

(65) Prior Publication Data

US 2024/0358271 A1 Oct. 31, 2024

(30) Foreign Application Priority Data

Apr. 28, 2023 (EP) .................................... 23170613

(51) Int. Cl.
*A61B 5/055* (2006.01)
*A61B 5/06* (2006.01)
*G01R 33/36* (2006.01)

(52) U.S. Cl.
CPC ................ *A61B 5/055* (2013.01); *A61B 5/06* (2013.01); *G01R 33/36* (2013.01)

(58) Field of Classification Search
CPC ............ A61B 5/055; A61B 5/06; G01R 33/36
See application file for complete search history.

(56) References Cited

U.S. PATENT DOCUMENTS 5,085,219 A 2/1992 Ortendahl et al.
5,519,321 A 5/1996 Hagen et al.
(Continued)

FOREIGN PATENT DOCUMENTS

CN 111077484 A 4/2020
JP H07327950 A 12/1995
(Continued)

*Primary Examiner* — Gregory H Curran
(74) *Attorney, Agent, or Firm* — Banner & Witcoff, Ltd.

(57) ABSTRACT

A local coil for a magnetic resonance apparatus, including: at least one antenna designed to receive radio frequency signals in a frequency and power range of a magnetic resonance measurement; a holding element designed to hold the at least one antenna in a position that is appropriate for application on a diagnostically relevant body region of a patient, wherein the at least one antenna is mechanically connected to the holding element; a base element, wherein a first end of the holding element is mechanically connected to the base element and wherein a second end of the holding element opposite the first end is free-floating; and a guide system that is mechanically connected to the base element and the holding element, and is designed to position the holding element variably with respect to the base element.

15 Claims, 9 Drawing Sheets

(56) References Cited

U.S. PATENT DOCUMENTS

| | | | | |
|---|---|---|---|---|
| 7,525,312 | B2 * | 4/2009 | Green | G01R 33/341<br>324/318 |
| 7,693,570 | B2 * | 4/2010 | Green | G01R 33/28<br>324/318 |
| 9,226,685 | B2 * | 1/2016 | Choe | A61B 5/4542 |

FOREIGN PATENT DOCUMENTS

| | | | |
|---|---|---|---|
| JP | 2006014751 | A | 1/2006 |
| WO | 2023041286 | A1 | 3/2023 |
| WO | 2023041288 | A1 | 3/2023 |
| WO | 2023041289 | A1 | 3/2023 |

* cited by examiner

LOCAL COIL AND MAGNETIC RESONANCE DEVICE

BACKGROUND

Independent of the grammatical term usage, individuals with male, female, or other gender identities are included within the term.

Diseases of the teeth and the periodontium, such as caries or periodontitis, are nowadays commonly diagnosed using X-ray-based imaging methods. Above all, conventional or digital X-ray projection methods, as well as recently also three-dimensional X-ray methods, are used. An example of a three-dimensional X-ray method is digital volume tomography, which can be used for imaging teeth and the viscerocranium.

A major disadvantage of X-ray methods is the need to use ionizing radiation for imaging. An imaging method that avoids ionizing rays is magnetic resonance tomography. This typically enables better soft tissue contrast than X-ray methods and supports three-dimensional imaging of an object to be examined as standard. Furthermore, magnetic resonance tomography enables an imaging of cysts as well as a detection of a degradation of dentin before this can be detected by an X-ray method. The magnetic resonance tomography is thus a potential alternative to known X-ray methods in the imaging of a dental region and/or a jaw region as well as the diagnosis of dental diseases.

Magnetic resonance tomography is a known imaging method that can be used to generate magnetic resonance images of an interior of the object to be examined. When performing magnetic resonance imaging, the object to be examined is usually positioned in a strong, static and homogeneous basic magnetic field (B0 magnetic field) of a magnetic resonance apparatus. The basic magnetic field can have magnetic field strengths of 0.2 Tesla to 7 Tesla, so that nuclear spins of the object to be examined are oriented along the basic magnetic field. In order to trigger so-called nuclear magnetic resonances, radio frequency signals, so-called excitation pulses (B1 magnetic field), are irradiated into the object to be examined. Each excitation pulse causes a deviation of a magnetization of certain nuclear spins of the object to be examined from the basic magnetic field by an amount that is also known as a flip angle. An excitation pulse can have an alternating magnetic field with a frequency that corresponds to the Larmor frequency at the respective static magnetic field strength. The excited nuclear spins can have a rotating and decaying magnetization (nuclear magnetic resonance), which can be acquired as a magnetic resonance signal by means of special antennas. For the purpose of spatial encoding of the nuclear spin resonances of the object to be examined, magnetic gradient fields can be superimposed on the basic magnetic field.

The received magnetic resonance signals are typically digitized and stored as complex values in a k-space matrix. This k-space matrix can be used as a basis for a reconstruction of magnetic resonance images as well as a determination of spectroscopy data. The reconstruction of a magnetic resonance image is typically carried out by means of a multidimensional Fourier transform of the k-space matrix.

At present, however, an application of magnetic resonance tomography for imaging teeth and/or the jaw apparatus is mainly limited to research studies. This is due, inter alia, to the fact that imaging techniques based on X-rays can be performed quickly and are associated with a negligible restriction of the patient. Conversely, a magnetic resonance examination can be associated with an increased effort with regard to the preparation and positioning of the patient. Furthermore, patients are sometimes greatly impaired by the placement in a patient tunnel (for example, in the case of closed or cylindrical magnetic resonance apparatuses) or the use of dedicated head coils. This circumstance can present a considerable challenge, especially in claustrophobic patients or children, and can lead to a premature termination of a magnetic resonance examination.

SUMMARY

It is, therefore, an object of the invention to provide a local coil that enables a capture of magnetic resonance images with high quality and reduces a restriction of a patient's comfort.

This object is achieved in accordance with the invention by the subjects of the independent claims. Advantageous aspects and expedient developments are the subject matter of the subordinate claims.

The local coil in accordance with the invention comprises at least one antenna, a base element, a holding element and a guide system.

The at least one antenna is designed so as to receive radio frequency signals in a frequency and power range of a magnetic resonance measurement. An antenna can be a coupling element between electromagnetic waves guided in signal conductors and unguided, i.e., located in a free space. The at least one antenna is designed, in particular, so as to receive electromagnetic waves in the region of a magnetic resonance frequency of a magnetic resonance-active atomic nucleus. Electromagnetic waves that are relevant for magnetic resonance measurements can be radio frequency signals (magnetic resonance signals), which comprise frequencies between 1 and 500 MHz, preferably between 10 and 300 MHz. The magnetic resonance signals of conventional atomic nuclei to be examined can have a low power of a few microwatts to several milliwatts.

A signal conductor is preferably an electrically conductive wire. The wire of the signal conductor can have an oval or polygonal cross section. The wire of the signal conductor is preferably designed so as to continuously transmit the powers that are specified above. It is also conceivable for the signal conductor to be designed as a conductor track on a printed circuit board. The signal conductor can be made of copper. However, other electrically conductive metals, such as gold, aluminum, and the like, are also conceivable.

Of course, the local coil in accordance with the invention can comprise multiple antennas. In this case, the antennas can be arranged spaced from one another, adjacent to one another, or partially overlapping. The antennas can further be arranged in the form of a grid or a matrix.

In a preferred aspect, the local coil has multiple antennas that are designed so as to receive magnetic resonance signals from a diagnostically relevant body region, in particular a head region or a jaw region of the patient.

The at least one antenna can be mechanically connected to a supporting structure and can be supported or held by this supporting structure. It is also conceivable for the at least one antenna to be integrated or embedded in the supporting structure. The supporting structure can have a material that is designed so as to provide touch protection for the patient and/or so as to be replicated in a contour of the diagnostically relevant body region of the patient.

It is conceivable that the local coil in accordance with the invention has a transmitting antenna that is designed so as to emit a radio frequency signal in a direction of the object to be examined, such as, for example, a jaw region of the patient. The radio frequency signal that is emitted by the transmitting antenna can be in a power range of a few watts to several kilowatts, for example, in dependence upon the basic magnetic field of a magnetic resonance apparatus. The radio frequency signal that is emitted by the transmitting antenna can, in particular, represent a B1 magnetic field. A part of the local coil having the transmitting antenna can, for example, represent a transmitting unit of the local coil. The transmitting antenna can coincide with the at least one antenna or be separate from the at least one antenna.

The at least one antenna is mechanically connected to the holding element. The holding element is preferably designed so as to enable positioning and/or orientation of the at least one antenna with respect to the patient and/or the base element. The holding element can, in particular, be designed so as to support the at least one antenna and/or to provide mechanical support for a third guide mechanism in accordance with an aspect described below.

The holding element is designed so as to hold the at least one antenna in a position that is appropriate for the application on a diagnostically relevant body region of a patient.

In one aspect, the at least one antenna is fastened in a detachable manner to the holding element. The holding element and the at least one antenna and/or the supporting structure of the at least one antenna can have a holding mechanism that is designed so as to mechanically connect the at least one antenna reversibly to the holding element. The holding element and the at least one antenna can, in particular, have complementary parts of the holding mechanism that are designed so as to engage in one another reversibly. For example, the holding mechanism can be designed as a plug-in connection, a snap-in connection, or a latching connection. In addition, however, other positive-locking and/or non-positive-locking mechanical connections are also conceivable.

The holding element is preferably mechanically connected to the base element. The mechanical connection between the holding element and the base element can be provided, for example, by means of the guide system. It is, in particular, conceivable that the mechanical connection between the holding element and the base element is provided by means of a first guide mechanism and/or a second guide mechanism of the guide system. The base element and the guide system are preferably designed so as to hold the holding element in an appropriate position for the application relative to a capture region that is defined by the base element.

A capture region that is defined by the base element can comprise a volume and/or a surface in which the diagnostically relevant body region of the patient is positioned appropriately for the application for a magnetic resonance examination. The capture region is preferably defined by a volume that is adjacent to a base surface of the base element and/or a volume that is delimited by the base element. The capture region can, in particular, be characterized by a free space that is suitable for capturing the diagnostically relevant body region of the patient in the local coil. The diagnostically relevant body region of the patient can, in particular, be a section of a head or a jaw region.

The base element can be mechanically connected to a component of a magnetic resonance apparatus, such as a patient table and/or a patient support apparatus, for example. The base element can furthermore have a positioning unit that is designed so as to position the base element relative to the magnetic resonance apparatus, the patient support apparatus and/or the patient. The base element can be understood to be a mechanical structure that is designed so as to hold the holding element robustly and/or reproducibly in the position that is appropriate for the application on the diagnostically relevant body region of the patient. The base element can further represent a mechanical interface between the magnetic resonance apparatus and the holding element.

The guide system is mechanically connected to the base element and the holding element and is designed so as to position the holding element variably with respect to the base element.

The guide system can comprise any guide mechanism that enables the holding element to be moved with respect to the base element. The guide system preferably comprises a joint, a bearing, a hinge, in particular a pivoting or folding mechanism, a rail guide, a linear guide, or a combination of these or comparable mechanisms. The guide system is preferably designed so as to enable a simple and/or time-efficient transfer of the local coil, in particular, the holding element and/or the at least one antenna, from an open position into a closed position.

An open position of the local coil can be characterized by a maximum or predetermined deflection of the holding element and/or the at least one antenna with respect to a support surface of the local coil. The open position can, in particular, represent a "loading position" of the local coil, which enables the diagnostically relevant body region of the patient to be positioned in a position that is appropriate for the application relative to the base element. It is conceivable that the holding element and/or the at least one antenna are positioned or arranged in an open position of the local coil in such a manner that it is rendered possible for the diagnostically relevant body region of the patient to access the capture region of the local coil.

A support surface of the local coil can represent a surface of the local coil that is surrounded or enclosed by the base element. The support surface is preferably designed so as to capture and/or mechanically support the diagnostically relevant body region of the patient in a position that is appropriate for the application for a magnetic resonance examination of the diagnostically relevant body region. It is also conceivable that the support surface represents a section of a patient table or a patient support apparatus that is enclosed and/or surrounded by the base element of the local coil. In particular, the support surface can be a surface in a capture region of the local coil that is positioned between two delimiting elements of the base element or is surrounded by the base element.

A closed position of the local coil can be characterized by a minimal deflection of the holding element and/or the at least one antenna with respect to the support surface. The closed position can, in particular, represent an "examination position," which is characterized by a relative position, which is appropriate for the application of the at least one antenna on the diagnostically relevant body region of the patient for a magnetic resonance measurement. A transfer of the local coil from the open position into the closed position can, in particular, comprise guiding the holding element and/or the at least one antenna in the direction of the support surface of the local coil. It is conceivable that, during the transfer of the local coil from the open position into the closed position, the holding element is moved or deflected by means of the guide system in a direction that faces the base element.

In accordance with the invention, a first end of the holding element is mechanically connected to the base element. A second end of the holding element opposite the first end is free-floating.

In accordance with an aspect described above, the first end of the holding element can be mechanically connected to the base element.

The local coil in accordance with the invention preferably has a free space or gap that separates the second end of the holding element from a point on the base element that is closest to the second end of the holding element. In particular, the free space or gap can separate the second end of the holding element from a closest point on a delimiting element (for example, a second delimiting element) of the base element. It is conceivable that the holding element delimits or encloses the capture region in an X-direction of the local coil only along a section. The free space is preferably designed so as to provide access to the capture region from a surrounding area of the local coil. The free space is, in particular, configured in such a manner that access to the capture region along a surface normal to the support surface is rendered possible. The free space can have a dimension of more than 2 cm, more than 4 cm, or more than 6 cm in an X-direction of the local coil.

The holding element can be designed, for example, as a cylindrical body, a prism, an arm, a tube, a beam, or a shaft. A diameter of the holding element is preferably small in comparison with a longitudinal extension of the holding element. For example, the diameter of the holding element can be less than 10 cm, less than 8 cm, or preferably less than 6 cm. In this manner, an impairment of a patient's view during a magnetic resonance examination using the local coil can be advantageously reduced.

The local coil in accordance with the invention is preferably designed as a dental coil that is designed so as to acquire magnetic resonance signals of a tooth region and/or a jaw region of a patient. The holding element can be designed so as to hold the at least one antenna of the local coil on an oral region and/or a cheek region of a patient. In particular, the holding element can be designed so as to hold the at least one antenna in a position that is appropriate for the application on the oral region and/or cheek region of the patient in such a manner that the at least one antenna is adapted to the oral region and/or the cheek region of the patient and/or at least partially surrounds this cheek region along a circumferential direction of the patient's head.

An open local coil can be provided by a holding element having a free-floating end. An open local coil offers numerous advantages over conventional local coils, such as, for example, improved access to the capture area, improved ventilation, avoidance of shading of the diagnostically relevant body region, but also reduced impairment of a patient's field of view. In this manner, the comfort of a patient during a magnetic resonance examination can be advantageously improved, and/or a risk of a termination of a magnetic resonance examination can be reduced.

In one aspect of the local coil in accordance with the invention, the guide system has a first guide mechanism that is designed so as to guide the holding element along an arcuate path relative to the base element.

An arcuate path can represent, for example, a section of a circular path or an elliptical path.

The first guide mechanism can be designed, for example, as a bearing, a joint, a hinge, or the like. It is conceivable that the first guide mechanism is designed so as to enable the holding element to be pivoted or rotated about a fixed or movable point, in particular, a bearing point or an axis center.

The first guide mechanism can be designed in particular so as to enable pivoting or rotation of the holding element having the at least one antenna about an X axis of the local coil.

A particularly time-efficient and/or easy-to-handle transfer of the local coil from the open position into the closed position can be realized by means of a first guide mechanism. In addition, a guide system in accordance with the invention can be advantageously implemented on one side of the base element of the local coil so that an impairment of the patient by components of the local coil in the field of view of the patient can be advantageously reduced.

In one aspect of the local coil in accordance with the invention, the guide system has a second guide mechanism that is designed so as to variably position the holding element relative to the base element essentially along a surface normal of a support surface that is defined by the base element.

A surface normal of the support surface is preferably oriented parallel to a Y direction of the local coil. The second guide mechanism can be designed so as to move the holding element having the at least one antenna at an angular deviation of less than 30°, less than 20° or less than 10° with respect to the surface normal of the support surface. The second guide mechanism can, in particular, be designed so as to position the holding element relative to the support surface and/or the base element.

The second guide mechanism can comprise any guide element, such as, for example, a rail, a groove, a rod, a tube, or the like. It is conceivable that an orientation of the guide element defines a positioning direction of the holding element having the at least one antenna.

In a preferred aspect, the first guide mechanism and the second guide mechanism of the guide system are mechanically connected and/or integrated. The first guide mechanism and the second guide mechanism can be designed in particular as a combined guide mechanism. For example, the second guide mechanism is designed so as to displace an axis or a bearing point of the first guide mechanism in order to adapt or adjust a movement trajectory of the holding element. However, it is also conceivable that the first guide mechanism is designed so as to change an alignment and/or orientation of the second guide mechanism, as a result of which the holding element and/or the at least one antenna can be positioned at an angular deviation of less than 30°, less than 20° or less than 10° with respect to the Y direction of the local coil.

The first guide mechanism and the second guide mechanism can be mechanically connected or integrated in such a manner that, during the change between the open position and the closed position of the local coil, the holding element can be guided successively along a movement trajectory that is defined by the first guide mechanism and a movement trajectory that is defined by the second guide mechanism.

In a further aspect, the guide mechanism and the second guide mechanism are mechanically connected or integrated in such a manner that a movement trajectory of the holding element essentially describes a section of an elliptical path when changing between the open position and the closed position of the local coil. The section of the elliptical path can, for example, correspond to a combined movement trajectory, which results from a superposition of a movement trajectory that is defined by the first guide mechanism and a movement trajectory that is defined by the second guide mechanism.

In particular, the first guide mechanism and/or the second guide mechanism provide a guide for the holding element.

This can mean that a movement of the holding element by means of the first guide mechanism and/or the second guide mechanism is limited to a predetermined number of spatial directions and/or directions of rotation. For example, the variable positioning of the holding element with respect to the base element by means of the first guide mechanism can be limited to moving the holding element along a circular path. Conversely, the variable positioning of the holding element with respect to the base element by means of the second guide mechanism can be limited to a movement along a straight line, in particular, a parallel to a Y direction of the local coil. Conversely, by means of the mechanical connection or integration of the first guide mechanism and the second guide mechanism, a variable positioning of the holding element and/or the at least one antenna along an elliptical path can be rendered possible, which results from a combination of the movement trajectories of the first guide mechanism and the second guide mechanism.

Due to the provision of a second guide mechanism, an additional degree of freedom of movement can be obtained when positioning the holding element and/or the at least one antenna by means of the guide system. As a result, an orientation of the at least one antenna relative to the diagnostically relevant body region of the patient can be advantageously simplified and/or accelerated.

Due to a mechanical connection or integration of the first guide mechanism and the second guide mechanism, a volume or installation space can be reduced in an advantageous manner compared to an aspect having mechanically separate guide mechanisms. As a result, it is possible to provide a particularly compact local coil, which is more open, offers greater freedom, and/or reduces an impairment of the patient during the magnetic resonance examination.

In one aspect, the local coil in accordance with the invention has a locking mechanism that is designed so as to enable positioning of the holding element by means of the guide system and/or so as to fix the guide system in a desired position.

The locking mechanism can have a locking element. The locking mechanism and/or the locking element are preferably mechanically coupled to the first guide mechanism and/or the second guide mechanism.

The locking mechanism can be designed so as to interrupt a force that is transmitted to the holding element by means of the first guide mechanism and/or the second guide mechanism when the locking element is in a predetermined position relative to the first guide mechanism and/or the second guide mechanism. The locking element can be designed, for example, as a stop element, such as, for example, a pin, a bolt, a plate, or a block, but also as a latching element, a spring element, a gear element, or a combination of such elements.

It is conceivable that the locking mechanism is designed so as to enable and/or prevent a movement of the holding element along a movement trajectory that is predefined by the first guide mechanism and/or the second guide mechanism.

The locking mechanism can also be designed so as to fix the first guide mechanism and/or the second guide mechanism in a desired position. In a preferred aspect, the locking mechanism is designed so as to prevent a movement of the holding element along the movement trajectory that is predetermined by the second guide mechanism.

The locking mechanism can, in particular, be designed so as to prevent a movement of the holding element by means of the second guide mechanism when the locking element is in a starting position. It is conceivable that the locking mechanism is designed so as to release the second guide mechanism due to a user exerting a manual force on the locking element so that the holding element can be variably positioned along the movement trajectory that is predefined by the second guide mechanism. The locking mechanism can, for example, have a spring element that is designed so as to return the locking element to the starting position when the application of force by the user has ended.

In a further aspect, the locking mechanism is designed so as to enable positioning of the holding element by means of the first guide mechanism and/or so as to fix the first guide mechanism in a desired position. The locking mechanism can, for example, have a second locking element that is designed so as to enable and/or prevent a movement of the holding element along a movement trajectory that is predefined by the first guide mechanism. It is also conceivable for the first guide mechanism and the second guide mechanism to be mechanically coupled or integrated. In this case, the locking mechanism is designed so as to enable and/or prevent a movement of the holding element along a movement trajectory that is predefined by the first guide mechanism and/or the second guide mechanism.

Due to providing a local coil in accordance with the invention with a locking mechanism, an unintentional movement of the holding element and/or the at least one antenna can be avoided. In this manner, a risk of a collision with the diagnostically relevant body region of the patient in the capture region of the local coil can be advantageously prevented.

A collision can be characterized by an undesired coming together or merging of the at least one antenna with the diagnostically relevant body region of the patient. A collision can require a movement of the at least one antenna and/or the holding element in the direction of the diagnostically relevant body region of the patient. It is, in particular, conceivable that the collision comprises a contact, a force effect, and/or a force transmission between the one antenna and the diagnostically relevant body region of the patient. Conversely, a contact between the at least one antenna and the diagnostically relevant body region, which takes place with a release by the locking mechanism, is considered a controlled contact and does not fall under the definition of a collision given above.

A locking mechanism in accordance with the invention can be mechanically coupled to the guide system in an advantageous manner. As a result, a holding element that is free-floating on one side can be provided, which improves access to the capture region of the local coil and/or reduces an impairment of the patient.

In one aspect of the local coil in accordance with the invention, the locking mechanism has an adaptation element that is designed so as to variably adjust a mechanical resistance of the guide system.

It is conceivable that the adaptation element comprises a tensioning element, such as, for example, a mechanical spring, an elastic block and/or a tension mechanism. It is also conceivable for the adaptation element to have a transmission with a predetermined force transmission. The clamping element can be designed so as to oppose a movement of the holding element by means of the first guide mechanism and/or the second guide mechanism with a predetermined force, in particular, an elastic restoring force. It is also conceivable that the adaptation element is designed so as to adjust a frictional resistance between parts of the first guide mechanism and/or parts of the second guide mechanism.

Due to providing a local coil in accordance with the invention with an adaptation element, a resistance of an adjustment of the at least one antenna relative to the diagnostically relevant body region can be advantageously adapted to the physical requirements of a user. Furthermore, the adaptation element can prevent an unintentional collision with the diagnostic body region of the patient, which can be advantageous when operating the local coil from one side.

In a preferred aspect, the local coil in accordance with the invention has a third guide mechanism that is designed so as to enable rotation of the at least one antenna about an axis of the third guide mechanism.

The third guide mechanism can have a hinge, a joint, or a bearing, in particular, a plain bearing, a rotary bearing, or a rolling bearing. In a preferred aspect, the third guide mechanism has a bearing that surrounds the outer circumference of a body of the holding element along a section. In particular, in accordance with an aspect described above, the holding element can have a cylindrical body. The third guide mechanism can enclose the cylindrical body of the holding element along a cylinder section on the outer circumference. However, it is also conceivable that the third guide mechanism is arranged at one end of the holding element or between two halves or parts of the holding element. For example, in such an arrangement, the holding element can be designed as a rotary bearing, which is mechanically connected to the holding element by means of a flange or a comparable connection.

In one aspect, the holding element has a cylindrical body, wherein the third guide mechanism is designed so as to enable the at least one antenna to rotate about an axis or an axis of symmetry of the cylindrical body of the holding element.

Due to the provision of a third guide mechanism, an angular position of the at least one antenna relative to the support surface of the local coil can be set independently of the guide system. As a result, the at least one antenna can be pivoted or rotated out of the capture region in an advantageous manner, as a result of which an openness and/or accessibility of the local coil is further improved.

In one further aspect, the local coil in accordance with the invention has a second locking mechanism that is designed so as to enable the at least one antenna to rotate about the axis of the third guide mechanism and/or so as to fix the third guide mechanism in a desired position.

The second locking mechanism can comprise a locking element and/or a clamping element in accordance with an aspect described above. The second locking mechanism can, in particular, be designed so as to variably adjust a mechanical resistance or a frictional resistance of the third guide mechanism. For example, the second locking mechanism is designed so as to variably adjust a required application of force for a movement of the at least one antenna along a movement trajectory that is defined by the third guide mechanism. In a preferred aspect, the second locking mechanism comprises an adjusting element, in particular an adjusting screw, which is designed so as to adjust the mechanical resistance of the third guide mechanism continuously or in discrete steps. The adjusting element can be mechanically coupled to a clamping element. An adjusting element can advantageously enable the user to adjust the locking mechanism.

The second locking mechanism is designed in particular so as to prevent or enable a relative movement between the holding element and the at least one antenna.

Due to providing a local coil in accordance with the invention with a second locking mechanism, a particularly easy-to-use and/or compact possibility for positioning the at least one antenna relative to the diagnostically relevant body region of the patient can be realized in an advantageous manner. As a result, an impairment of the patient can be reduced, and/or operation of the local coil in accordance with the invention can be simplified from one side.

In one aspect, the local coil in accordance with the invention has a fourth guide mechanism. The fourth guide mechanism is mechanically connected to the holding element and is designed so as to variably position an auxiliary element along a tangent to a surface of the holding element.

The fourth guide mechanism preferably has a guide element, such as, for example, a rail guide, a telescopic guide or a linear guide. The guide element can be designed so as to position the auxiliary element along the tangent to the surface of the holding element. In particular, the tangent to the surface of the holding element can be oriented parallel to a Z direction of the local coil. An orientation of the tangent and the surface of the holding element can coincide with an extension direction of the guide element.

The fourth guide mechanism can further comprise a guide mechanism in accordance with an aspect of the third guide mechanism. As a result, a rotation of the fourth guide mechanism about an axis of the holding element can additionally be enabled, as a result of which the aid can be positioned in an advantageous manner more accurately relative to the diagnostically relevant body region of the patient.

The fourth guide mechanism is preferably designed so as to move and/or position the auxiliary element independently of the third guide mechanism. In one aspect, the third guide mechanism and the fourth guide mechanism are connected to the holding element separately from one another.

It is conceivable that an orientation of the tangent that is defined by the fourth guide mechanism with the surface of the holding element is fixed by means of a mechanical connection between the fourth guide mechanism and the holding element. For example, the fourth guide mechanism can comprise a clamp or a comparable mechanical connection, which connects the fourth guide mechanism to the holding element in a predetermined orientation.

An auxiliary element can be any apparatus that enables and/or supports the acquisition of magnetic resonance signals of the diagnostically relevant body region of the patient. In a preferred aspect, the auxiliary element comprises a mirror element that can be variably positioned along a Z direction of the local coil by means of the fourth guide mechanism.

Due to providing a local coil in accordance with the invention with a fourth guide mechanism, it is possible to connect an auxiliary element in an advantageous manner to the holding element and to position the auxiliary element independently of the orientation of the at least one antenna relative to the diagnostically relevant body region of the patient. A mirror element can advantageously expand a field of view of the patient and, in particular in the case of children and/or claustrophobic patients, reduce the risk of a termination of the magnetic resonance measurement.

In a further aspect of the local coil in accordance with the invention, the base element has two delimiting elements that flank a capture region from two opposite sides, said capture region being defined by the base element.

The guide system, in particular the first guide mechanism and/or the second guide mechanism, is preferably coupled to exactly one delimiting element or is mechanically connected to exactly one delimiting element. It is, in particular, conceivable that the guide system and the holding element are carried by exactly one delimiting element. The one delimiting element can, in particular, be designed as a carrier structure or a carrier arm for the guide system and the holding element.

In accordance with the invention, a height of a first delimiting element exceeds a height of a second delimiting element.

It is conceivable that the second delimiting element and the holding element having the at least one antenna are separated from one another by a free space, so that a collision of the at least one antenna with the second delimiting element is avoided during the transfer of the local coil into the closed position.

The two delimiting elements of the base element can flank or at least partially enclose the diagnostically relevant body region of the patient from two opposite sides when the patient is positioned appropriately for the application relative to the local coil.

Due to the provision of a first delimiting element, a one-sided holding structure for the holding element can be realized in an advantageous manner, so that the second end of the holding element can be designed so as to be free-floating. A lower second delimiting element can advantageously enlarge a free space or gap between the holding element and a nearest point of the base element, as a result of which access to the capture region and/or an openness of the local coil to conventional local coils can be improved.

In one aspect of the local coil in accordance with the invention, the second delimiting element and the holding element are separated from one another by a free space or gap. The free space extends along a surface normal of a support surface that is defined by the base element in the direction of a capture region of the local coil.

It is conceivable that the free space is characterized by a free volume or an unobstructed space. The free space can also be defined by a gap that separates or spaces the second delimiting element and the holding element having the at least one antenna from one another. The free space preferably extends over an entire dimension of the base element in the Z direction of the local coil, over a width of the gap that separates the holding element and the at least one antenna from the second delimiting element, and over an entire height of the local coil in a Y direction.

Due to providing a local coil in accordance with the invention with a free space, access to the capture region or the diagnostically relevant body region and/or an openness of the local coil to conventional local coils can be improved in an advantageous manner. As a result, an efficiency and/or a reproducibility of a positioning of the at least one antenna on the diagnostically relevant body region of the patient can be improved in an advantageous manner.

In accordance with one aspect of the local coil in accordance with the invention, at least one delimiting element comprises a grip element.

It is conceivable that the first delimiting element and/or the second delimiting element have a grip element. The grip element is preferably designed so as to enable transport of the local coil, in particular lifting, lowering and/or aligning of the local coil, by a user.

A grip element can be provided, for example, by a recess in the at least one delimiting element. However, it is also conceivable that the grip element is designed as a dedicated grip piece, such as a knob, a rod, or a bracket.

Due to providing a local coil in accordance with the invention with a grip element, additional accessories for handling and/or transporting the local coil can be omitted in an advantageous manner. Furthermore, by providing a recess in the at least one delimiting element, an openness of the local coil can be further improved.

In one aspect, the local coil in accordance with the invention has a support element that is connected to the base element in a position that is appropriate for the application and is designed so as to stabilize the diagnostically relevant body region that is positioned in a capture region that is defined by the base element in a predetermined position with respect to the local coil.

The support element can be connected to the base element by means of a mechanical connection. The mechanical connection can in particular be designed as a positive-locking, a non-positive locking and/or a material connection.

The support element preferably has a shape that stabilizes the diagnostically relevant body region in the predetermined position with respect to the local coil. This can mean that the support element is designed so as to prevent, hinder, and/or obstruct a movement of the patient, in particular of the diagnostically relevant body region. The support element can, for example, have a depression and/or a recess that is designed so as to receive the diagnostically relevant body region. A surface of the support element can be replicated in accordance with a contour of the diagnostically relevant body region. It is also conceivable that the support element is designed so as to support the diagnostically relevant body region at dedicated points. In exemplary aspects, the support element can be designed as a neck roller, a U-shaped cushion, or a shell-shaped cushion.

In one aspect, the support element has an elastic material. Examples of elastic materials are elastomers, in particular plastics based on polyethene, polyurethane, polyamide, and polyester. In addition, materials on a natural basis, such as, for example, rubber or elastic fiber materials, are also conceivable. In a preferred aspect, the elastic material is a foam. A support element having an elastic material can advantageously have a low weight. Furthermore, a support element having an elastic material can adapt to a shape or surface contour of the diagnostic body region of the patient and thus cause an immobilization of the diagnostically relevant body region.

The first delimiting element and the second delimiting element are designed so as to hold the support element in a position that is appropriate for the application in the local coil by means of elastic restoring forces of the elastic material.

The support element can be connected to the base element in such a manner that the support element is elastically deformed by a positioning between the two delimiting elements. Due to the elastic deformation, elastic restoring forces can be built up in the support element, which prevents or complicates a slipping or an unintentional movement of the support element relative to the base element. In particular, the two delimiting elements can be arranged at an angle to one another in order to provide a positive-locking connection between the support element and the two delimiting elements.

By way of a local coil in accordance with the invention having a support element, the diagnostically relevant body region can be immobilized in an advantageous manner (i.e., a movement of the diagnostically relevant body region of the patient during an imaging examination can be reduced) without impairing a field of view and/or a face region of the patient.

In a preferred aspect of the local coil in accordance with the invention, the holding element and/or the base element comprise an electrical interface that is designed so as to connect the at least one antenna to a receiving unit of a magnetic resonance apparatus.

The electrical interface can comprise an electronic circuit. The electronic circuit can comprise an electronic component or a combination of multiple electronic components, such as, for example, transistors, resistors, capacitors, diodes, conductor tracks and the like. The electronic circuit can, in particular, have a protection circuit that is designed so as to protect the at least one antenna against overload. For the avoidance of magnetic attractive forces, standing waves, heating and comparable, undesirable effects, the electronic circuit can have a high proportion of non-magnetic materials and corresponding sheath wave barriers and/or baluns. The electronic circuit preferably has a printed circuit board (PCB) or a comparable substrate that is suitable for receiving the electronic components in a predetermined position with respect to one another.

In a preferred aspect, the electrical interface has a first terminal connection. It is conceivable that the receiving unit of the magnetic resonance apparatus can be connected to the first terminal connection by means of a signal line, for example an electrical terminal connection line. The electrical interface can furthermore have a second terminal connection. The second terminal connection can be electrically connected to the at least one antenna by means of a signal line. The at least one antenna and/or the receiving unit of the magnetic resonance apparatus can preferably be reversibly connected to the electrical interface. A reversible electrical connection can be provided, for example, by a plug/socket principle.

Due to providing a local coil in accordance with the invention with an electrical interface, a direct electrical terminal connection line between the at least one antenna and the receiving unit can be omitted in an advantageous manner. As a result, a mechanical resistance of the electrical terminal connection line, which can interfere with a movement of the at least one antenna, can be advantageously avoided. In addition, an impairment of the patient by an electrical terminal connection line in the capture region of the local coil can be advantageously prevented.

The magnetic resonance apparatus in accordance with the invention comprises a local coil in accordance with an aspect described above. In a preferred aspect, the local coil is mechanically connected to a patient table and/or a patient support apparatus of the magnetic resonance apparatus. The magnetic resonance apparatus and/or the local coil can, in particular, have a positioning unit that is designed so as to position the local coil relative to the magnetic resonance apparatus, the patient, and/or the patient positioning apparatus. The local coil comprises at least one antenna, a base element, a holding element, and a guide system in accordance with an aspect described above. The magnetic resonance apparatus is designed to acquire magnetic resonance data of a diagnostically relevant body region of a patient by means of the local coil.

In addition, the magnetic resonance apparatus in accordance with the invention has at least one electrical terminal connection line that is designed so as to electrically connect the at least one antenna of the local coil to the magnetic resonance apparatus, in particular, a receiving unit of the magnetic resonance apparatus.

In one aspect, the local coil has one or multiple transmitting antennas that are designed as one transmitting unit. The transmitting unit can be connected to a radio frequency unit of the magnetic resonance apparatus by means of an electrical terminal connection line, for example, via an electrical interface in accordance with an aspect described above. It is conceivable that the radio frequency unit provides an alternating current that is emitted as a radio frequency signal from the transmitting unit into a volume of the diagnostically relevant body region of the patient so that a B1 magnetic field is generated.

In a further aspect, the local coil has one or multiple antennas that are designed so as to receive magnetic resonance signals of the diagnostically relevant body region of the patient. The at least one antenna can be connected to a receiver channel of the magnetic resonance apparatus by means of an electrical terminal connection line. The at least one antenna is preferably connected to an electrical interface in accordance with an aspect described above by means of an electrical terminal connection line. The electrical interface can be designed so as to transmit a magnetic resonance signal that is received by the at least one antenna to the receiving unit of the magnetic resonance apparatus by means of a further electrical terminal connection line or signal line. The magnetic resonance apparatus is thus able to receive magnetic resonance signals of the diagnostically relevant body region of the patient and to reconstruct magnetic resonance images in dependence upon the received magnetic resonance signals.

By way of the magnetic resonance apparatus in accordance with the invention, a time-efficient and reproducible acquisition of magnetic resonance images of the jaw region of the patient can be rendered possible. In addition, the magnetic resonance apparatus in accordance with the invention shares the advantages of the local coil in accordance with the invention in accordance with an aspect described above.

BRIEF DESCRIPTION OF THE DRAWINGS

Further advantages and details are provided in the description below of exemplary aspects in conjunction with the drawings. In the drawings.

DETAILED DESCRIPTION

Figure 1:
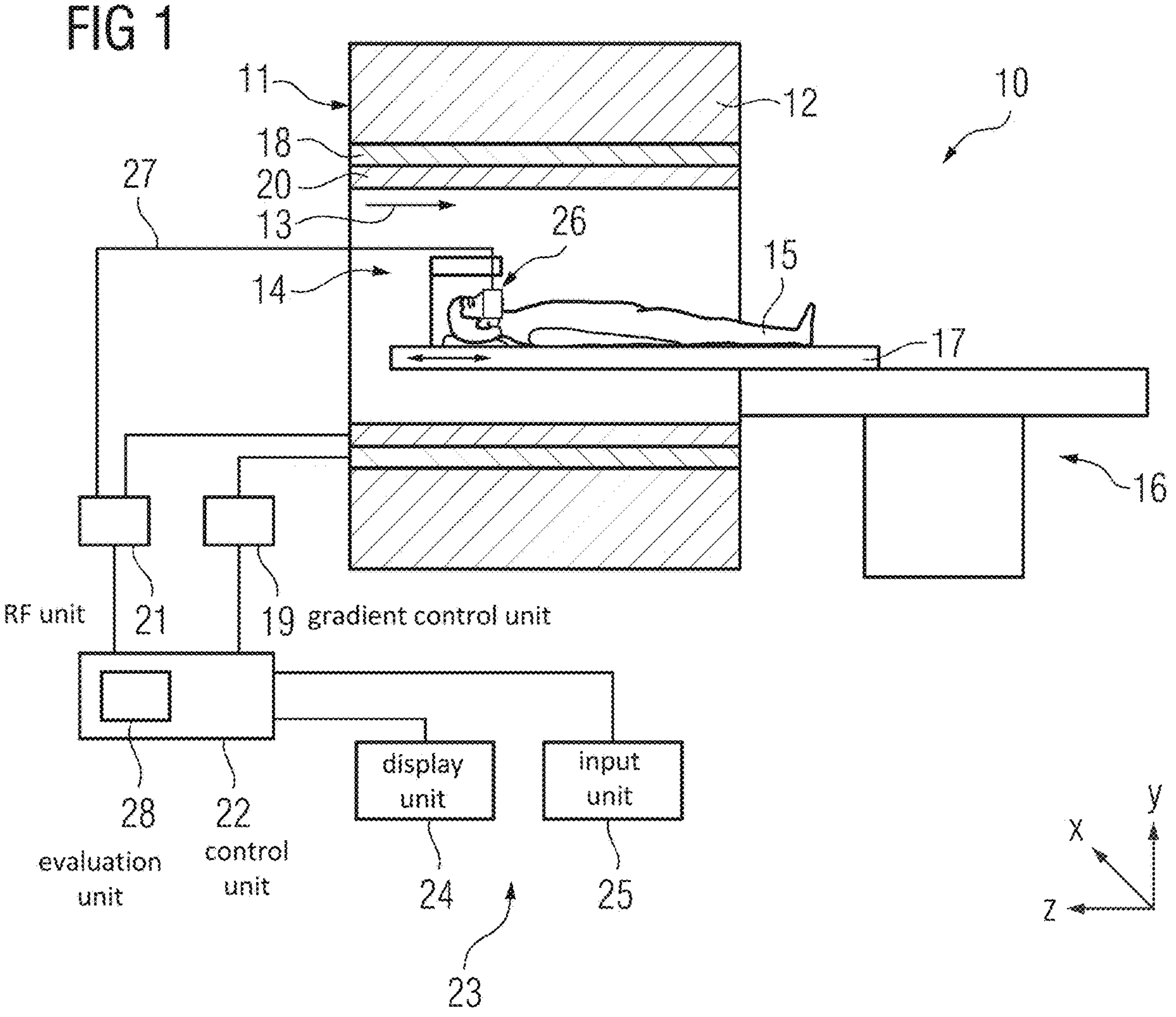
FIG. 1 shows a schematic representation of an aspect of a magnetic resonance apparatus in accordance with the invention.

In FIG. 1, a possible aspect of a magnetic resonance apparatus 10 in accordance with the invention having a local coil 26 in accordance with the invention is illustrated schematically. The magnetic resonance apparatus 10 comprises a magnet unit 11, which has, for example, a permanent magnet, an electromagnet, or a superconducting main magnet 12 for generating a strong and, in particular, homogeneous basic magnetic field 13 (B0 magnetic field). In addition, the magnetic resonance apparatus 10 has a patient receiving region 14 for receiving a patient 15. In the present exemplary aspect, the patient receiving region 14 is designed as cylindrical and is surrounded in a circumferential direction by the magnet unit 11 in the form of a cylinder. In principle, however, aspects of the magnetic resonance apparatus 10 and/or of the patient receiving region 14 that deviate from this example are also conceivable.

The magnetic resonance apparatus 10 preferably has a patient positioning apparatus 16, which is designed so as to position the patient 15 in the patient receiving region 14. For this purpose, the patient positioning apparatus 16 has a patient table 17 that is designed so as to be movable within the patient receiving region 14.

In the aspect that is illustrated in FIG. 1, the magnet unit 11 has a gradient coil 18 for generating magnetic gradient fields, which are used for spatial encoding during a magnetic resonance measurement. The gradient coil 18 is controlled by means of a gradient control unit 19 of the magnetic resonance apparatus 10. The magnet unit 11 can furthermore comprise a radio frequency antenna, which in the illustrated example is designed as a body coil 20 that is permanently integrated into the magnetic resonance apparatus 10. The body coil 20 is designed so as to excite atomic nuclei that are located in the basic magnetic field 13 that is generated by the main magnet 12. The body coil 20 is controlled by a radio frequency unit 21 of the magnetic resonance apparatus 10 and radiates radio frequency signals into an examination space, which is essentially formed by a patient receiving region 14 of the magnetic resonance apparatus 10. The body coil 20 can also be designed so as to receive magnetic resonance signals.

In the present case, the magnetic resonance apparatus 10 has a control unit 22 that is designed so as to control and/or coordinate the main magnet 12, the gradient control unit 19, and the radio frequency unit 21. The control unit 22 is preferably designed so as to control the execution of a sequence, such as, for example, an imaging gradient echo sequence, a TSE sequence, or a UTE sequence. The control unit 22 can comprise an evaluation unit 28, which is designed to evaluate digitized magnetic resonance signals that are acquired during a magnetic resonance measurement.

The magnetic resonance apparatus 10 can further comprise a user interface 23 that has a signal connection to the control unit 22. Control information such as imaging parameters, for example, and reconstructed magnetic resonance images can be displayed on a display unit 24, for example, on at least one monitor of the user interface 23 for a user. Furthermore, the user interface 23 has an input unit 25 by means of which parameters of a magnetic resonance imaging can be input by the user.

The magnetic resonance apparatus 10 comprises a local coil 26 in accordance with the disclosure, which in the present case is positioned on a head or a jaw region of the patient 15. The local coil 26 is designed so as to acquire magnetic resonance signals from a volume of the jaw region and to transmit them to the magnetic resonance apparatus 10. The local coil 26 preferably has an electrical terminal connection line 27 that provides a signal connection between an antenna 32 of the local coil and a receiving unit of the magnetic resonance apparatus 10, in particular the radio frequency unit 21 and/or the control unit 22.

One or multiple antennas 32 of the local coil 26 can also be electrically connected to an electrical interface 44 (see FIG. 4) of the local coil 26. The electrical interface 44 can, in turn, be connected to the receiving unit of the magnetic resonance apparatus 10 by means of the electrical terminal connection line 27 shown (see FIG. 1). Alternatively, the local coil 26 can be connected to the magnetic resonance apparatus 10 by means of a wireless signal connection.

Analogous to the body coil 20, the local coil 26 can also be designed so as to excite atomic nuclei and so as to receive magnetic resonance signals. For example, in order to emit radio frequency signals, a transmitting unit of the local coil 26 is driven by the radio frequency unit 21.

The illustrated magnetic resonance apparatus 10 can, of course, comprise further components that magnetic resonance apparatuses usually have. It is also conceivable that the magnetic resonance apparatus 10 has a C-shaped, a triangular or an asymmetrical structure of the magnetic field-generating components in lieu of the cylindrical structure. The magnetic resonance apparatus 10 can, in particular, be a dedicated magnetic resonance apparatus 10 that is designed so as to perform a magnetic resonance imaging of the jaw region of a standing or sitting patient 15.

Figure 2:
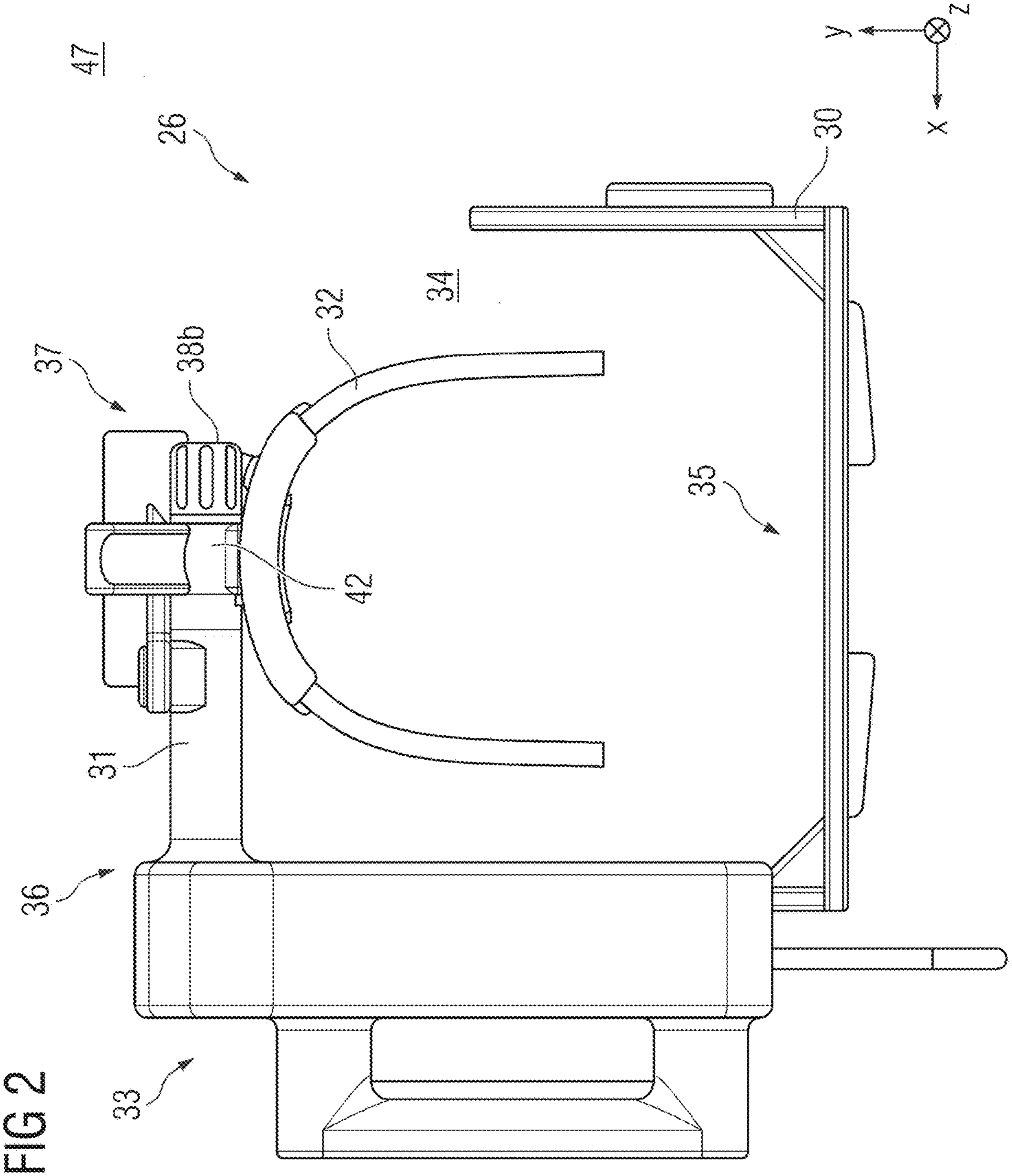
FIG. 2 shows a representation of an aspect of a local coil in accordance with the invention.

FIG. 2 illustrates an exemplary aspect of the local coil 26 in accordance with the disclosure. One or multiple antennas 32 of the local coil 26 are embedded in a carrier structure and are carried by a holding element 31. The holding element 31 can be positioned relative to the base element 30 by means of the guide system 33. One or multiple of the antennas 32 can form a transmitting unit and/or a receiving unit of the local coil 26. In the present case, the holding element 31 is designed as an arm having an essentially cylindrical body and is mechanically connected to the guide system 33 or the base element 30 at the first end 36. The second end 37 of the holding element 31 opposite the first end 36 is free-floating. This provides a free space 34 that facilitates access to a body region (not shown) that is positioned in the capture region 35. In the same way, an impairment of a patient 15 positioned in the capture region 35 can be reduced in comparison with conventional local coils.

In the illustrated aspect, the local coil 26 has a guide mechanism 42 that is designed so as to enable rotation of the antenna 32 about an axis of the guide mechanism 42. In the illustrated example, the guide mechanism 42 is mounted so as to be rotatable about a cylindrical section of the holding element 31 and enables the antenna 32 to rotate about the X axis of the local coil 26.

In the illustrated example, the local coil 26 also has a locking mechanism **38*b* that is designed so as to lock the antenna 32 in a desired rotational position with respect to the holding element 31 and/or so as to adjust a mechanical resistance of the guide mechanism 42. In the present case, the locking element 38*b* has an adjusting screw, which enables a user to adjust the mechanical resistance of the guide mechanism 42**.

Figure 3:
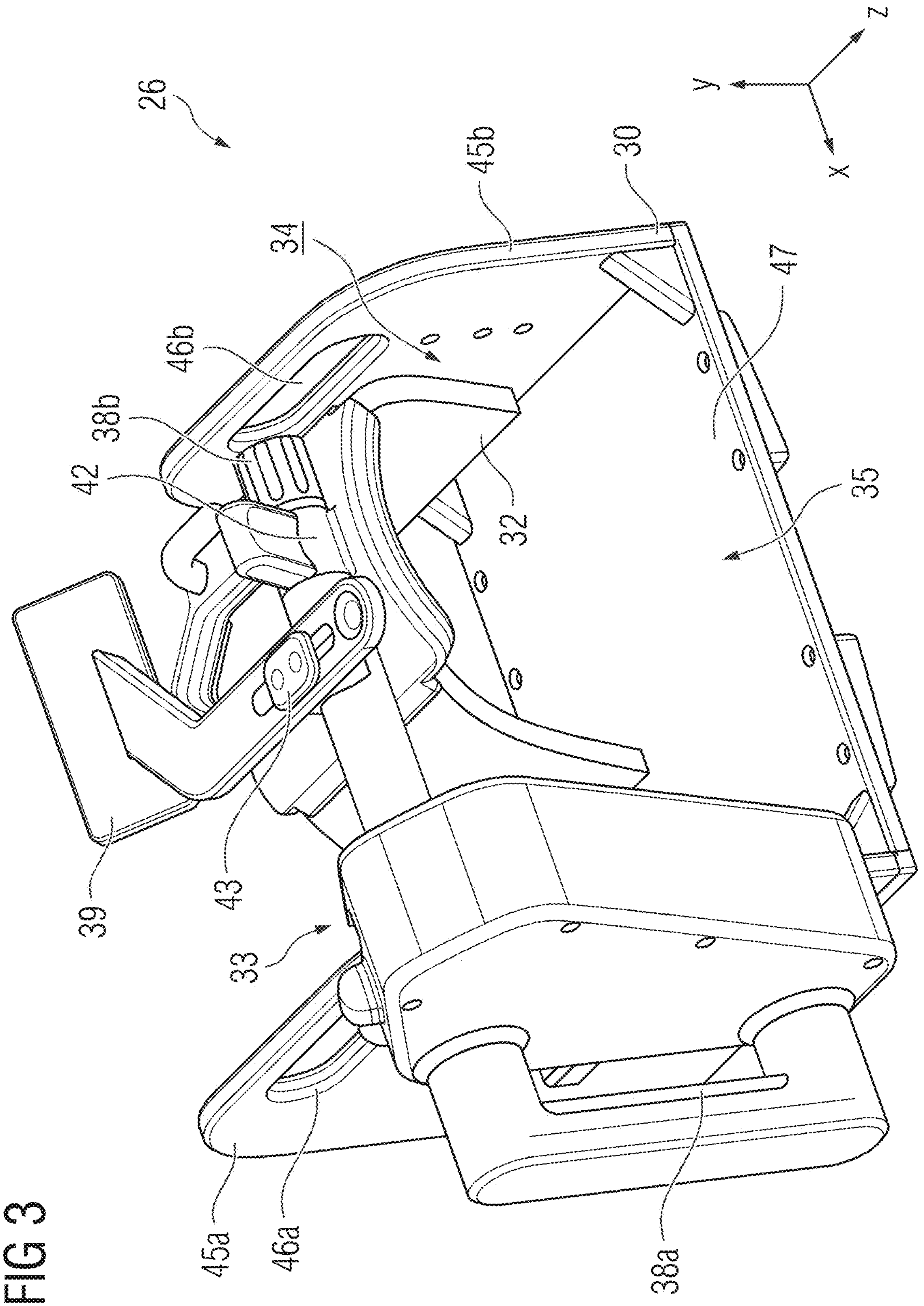
FIG. 3 shows a representation of an aspect of a local coil in accordance with the invention.

FIG. 3 shows an aspect in which the local coil 26 has a guide mechanism 43. The guide mechanism 43 is designed so as to variably position an auxiliary element 39 along a tangent to a surface of the holding element 31. The guide mechanism 43 is preferably designed so as to position the auxiliary element 39 along a Z direction of the local coil 26.

The guide mechanism 43 can be mechanically connected to the holding element 31 in a predetermined orientation. However, it is also conceivable that the guide mechanism 43 has a bearing (not shown), analogous to the guide mechanism 42, which enables the auxiliary element 39 to rotate about an axis or a circumference of the cylindrical body of the holding element 31. The guide mechanism 412 and the guide mechanism 43 are preferably designed so as to be mechanically independent of one another so that the antenna 32 and the auxiliary element 39 can be positioned independently of one another.

The base element 30 of the local coil 26 that is illustrated in FIG. 3 has two delimiting elements 45*a* and 45*b* (45*a*-*b*) that flank the capture region 35 from two opposite sides, said capture region being defined or surrounded by the base element 30. Starting from the support surface 47, the height of the first delimiting element 45*a* exceeds the height of the second delimiting element 45*b*, so that a collision of the holding element 31 and/or the antenna 32 with the second delimiting element 45*b* is avoided during the transfer of the local coil 26 into the illustrated closed position, and an additional free space is provided that facilitates access to the capture region 35 from a surrounding area 47 of the local coil 26. The delimiting elements 45*a*-*b* can have grip elements 46*a* and 46*b* in order to enable transport and/or orientation of the local coil 26 relative to the patient positioning apparatus 16 and/or the patient table 17 by a user.

In one aspect, the local coil 26 can have a support element (not shown) that is positioned on the support surface 47 in the capture region 35 appropriately for the application. The support element preferably comprises an elastic material. A dimension of the support element in the X direction can exceed a dimension of the capture region 35 in the X direction so that the support element is clamped between the delimiting elements 45*a*-*b* and is held in the position that is appropriate for the application by means of elastic restoring forces of the elastic material. The delimiting elements 45*a*-*b* can, in particular, be arranged at an angle to one another so that the free ends of the delimiting elements 45*a*-*b* have a smaller distance from one another than the ends of the delimiting elements 45*a*-*b* that are connected to the base element 30. This can improve clamping of the support element between the delimiting elements 45*a*-*b*.

Figure 4:
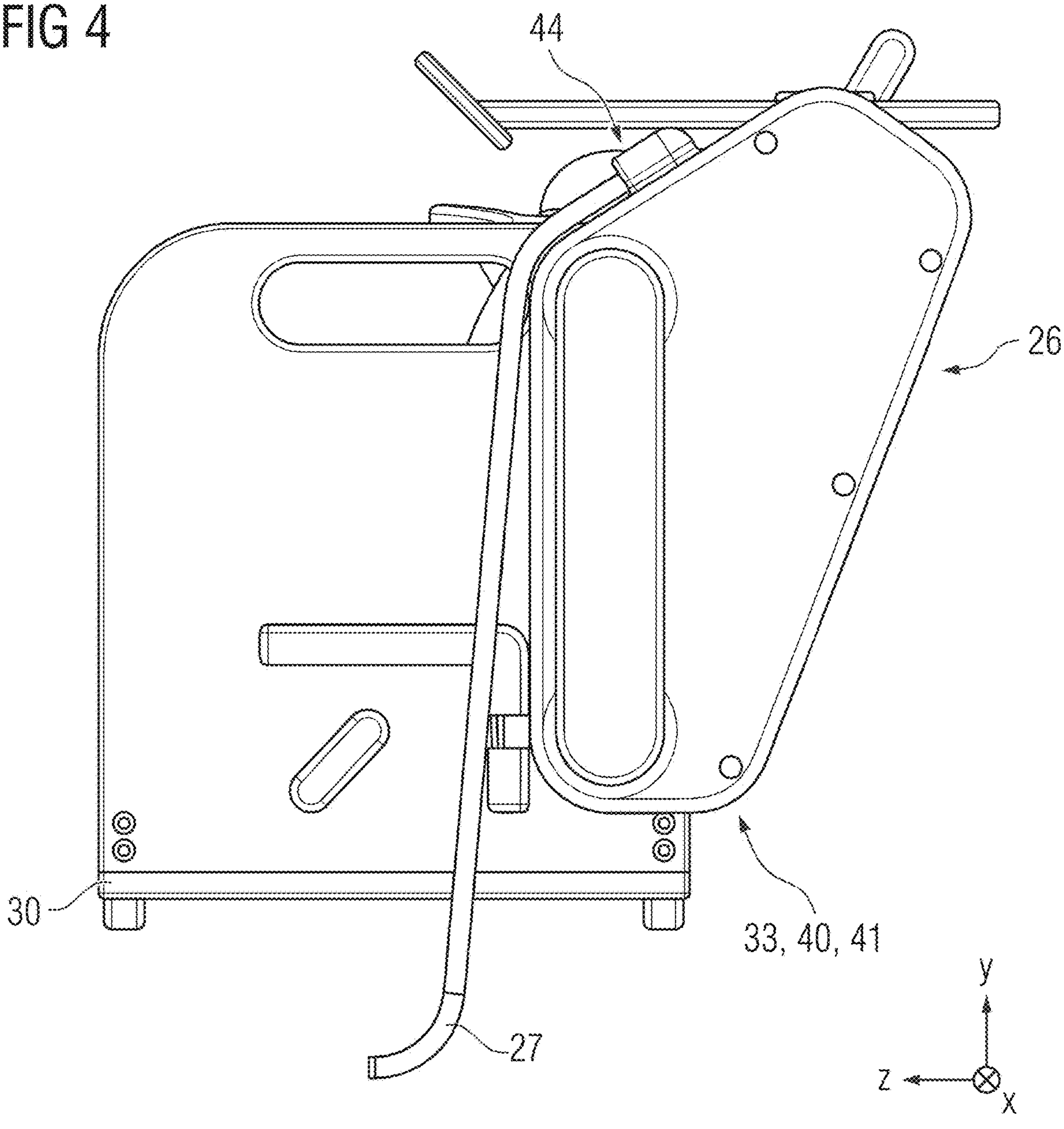
FIG. 4 shows a representation of an aspect of a local coil in accordance with the invention.

FIG. 4 illustrates an aspect of the local coil 26 in accordance with the disclosure having an electrical interface 44. The receiving unit of the magnetic resonance apparatus 10 can be connected to a first terminal of the electrical interface 44 by means of the electrical terminal connection line 27, while the antenna 32 is connected to a second terminal of the electrical interface 44 (not shown). The second connection of the electrical interface 44 is preferably integrated into the holding element 31 so that a routing of cables (or electrical lines) through a volume of the capture region 35 between the base element 30 and the holding element 31 is avoided.

In FIG. 4, the local coil 26 in accordance with the disclosure is in a closed position, i.e. the antenna 32 is deflected in the direction of the support surface 47 (see FIG. 3) of the local coil 26 by means of the guide mechanism 41 of the guide system 33. In the present case, the guide mechanism 41 is designed so as to position the holding element 31 variably along the Y direction of the local coil 26.

Figure 5:
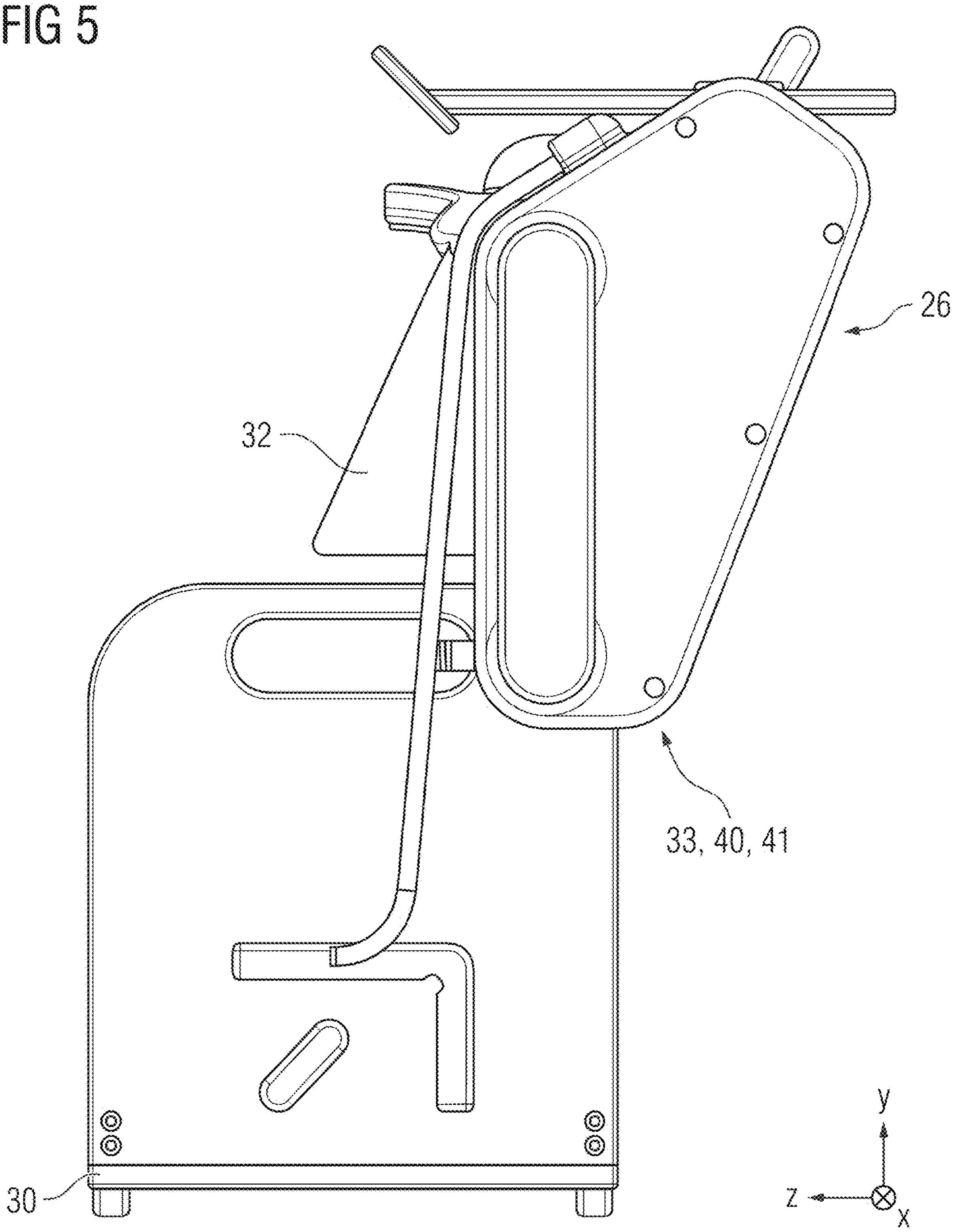
FIG. 5 shows a representation of an aspect of a local coil in accordance with the invention.

Conversely, in FIG. 5, the local coil 26 in accordance with the disclosure is in an open position, i.e. the antenna 32 is deflected in a direction opposite to the support surface 47 of the base element 30 by means of the guide mechanism 41 of the guide system 33. The guide mechanism 41 can, in particular, be a second guide mechanism in accordance with an aspect described above.

Figure 7:
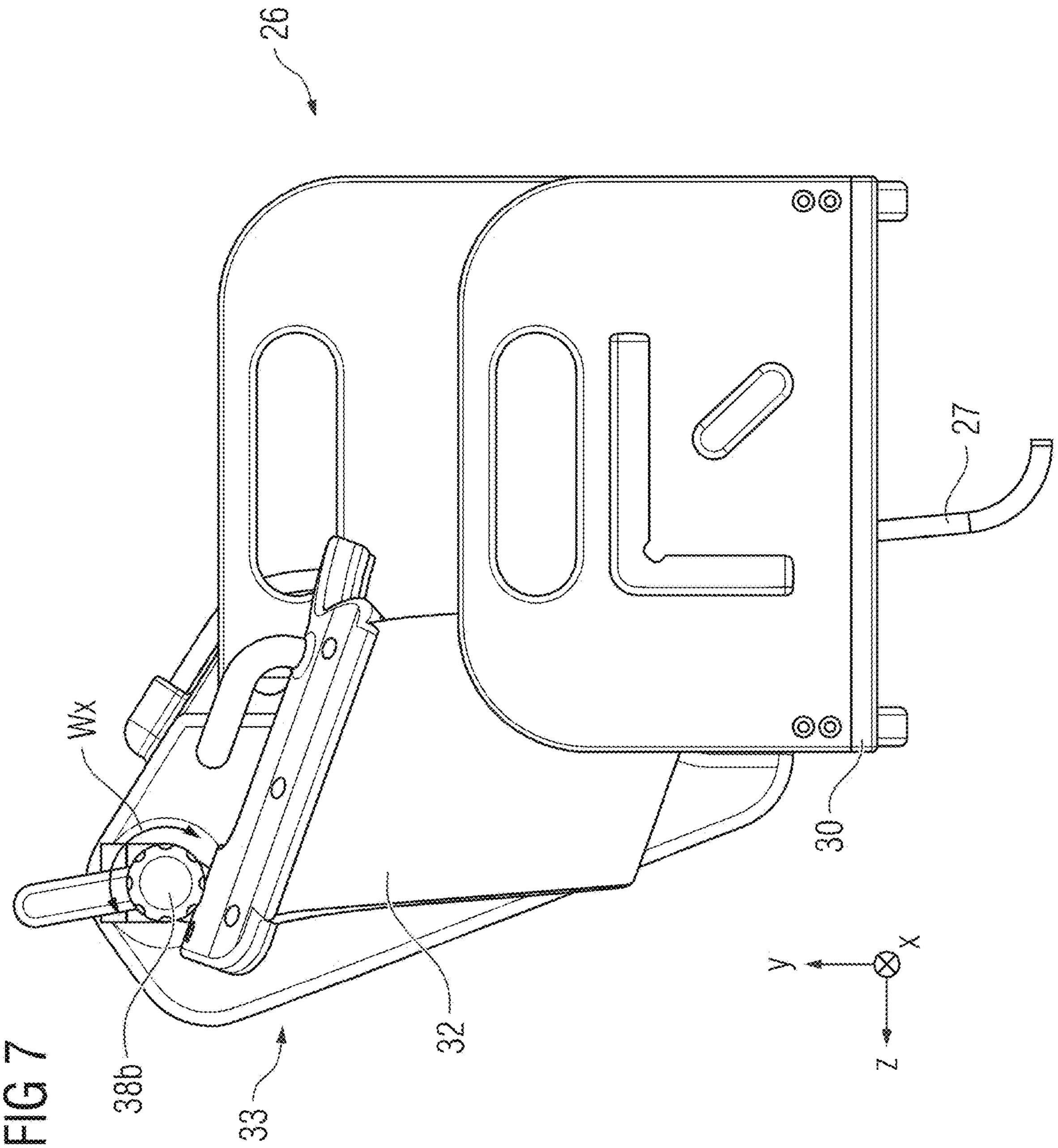
FIG. 7 shows a representation of an aspect of a local coil in accordance with the invention.
Figure 8:
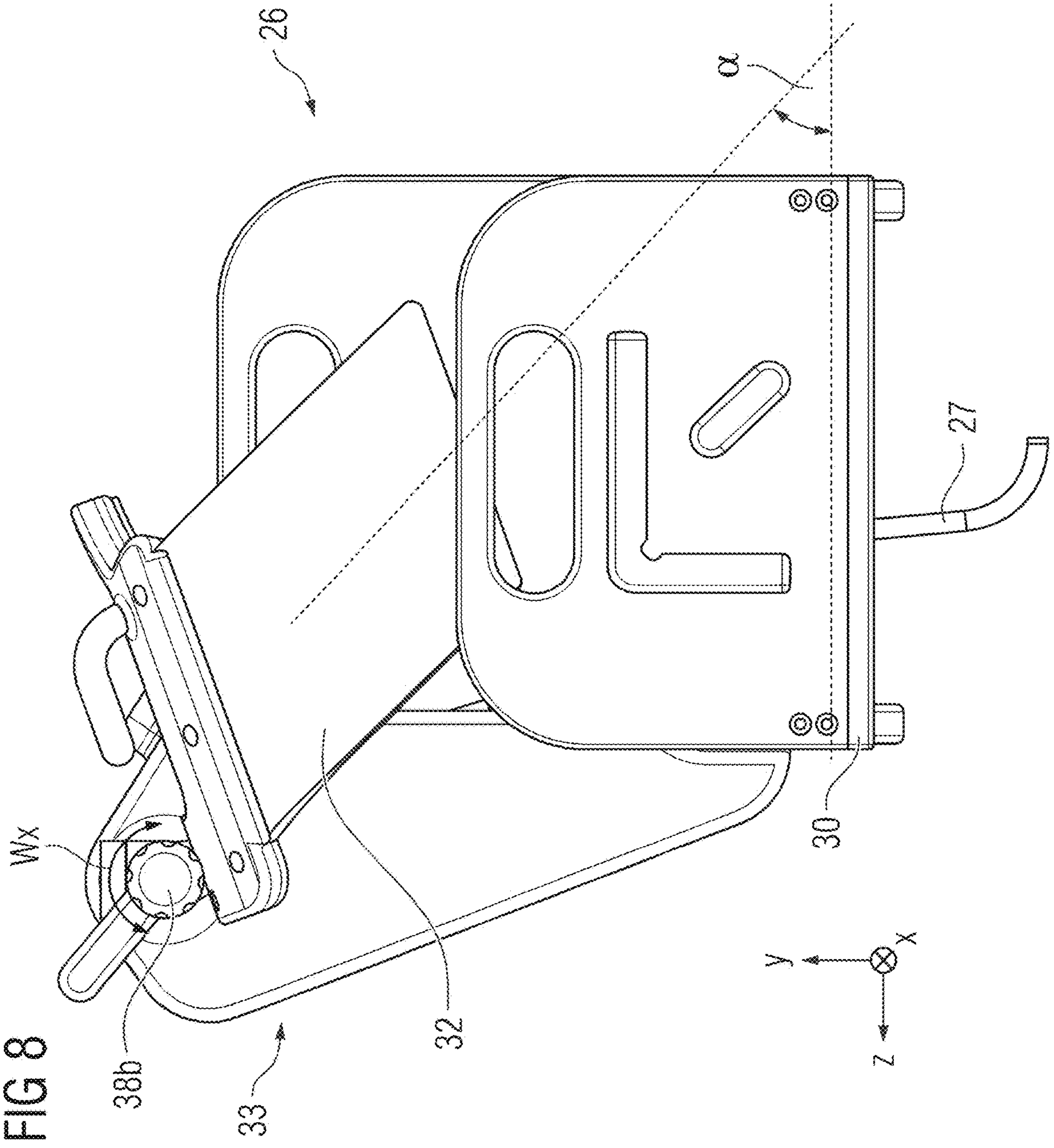
FIG. 8 shows a representation of an aspect of a local coil in accordance with the invention.

In a preferred aspect of the local coil 26 in accordance with the disclosure, a transfer of the local coil 26 from the closed position into the open position is only possible when the at least one antenna 32, as shown in FIGS. 7 and 8, has been transferred from a measuring position into a starting position by means of the guide mechanism 42. In the measurement position, the antenna 32 can be oriented essentially in the Y direction and/or in the direction of the capture region 35 (cf. FIG. 7). Conversely, in the starting position, the antenna 32 can be oriented at least partially in the Z direction, for example with an inclination at an angle α (cf. FIG. 8).

It is conceivable that the local coil 26 has a securing mechanism that prevents the local coil 26 from being transferred from the closed position into the open position or vice versa if an inclination of the antenna 32 to the Z axis or the support surface 47 falls below a predetermined angle α, e.g., 30° or 40° or 50°.

Figure 6:
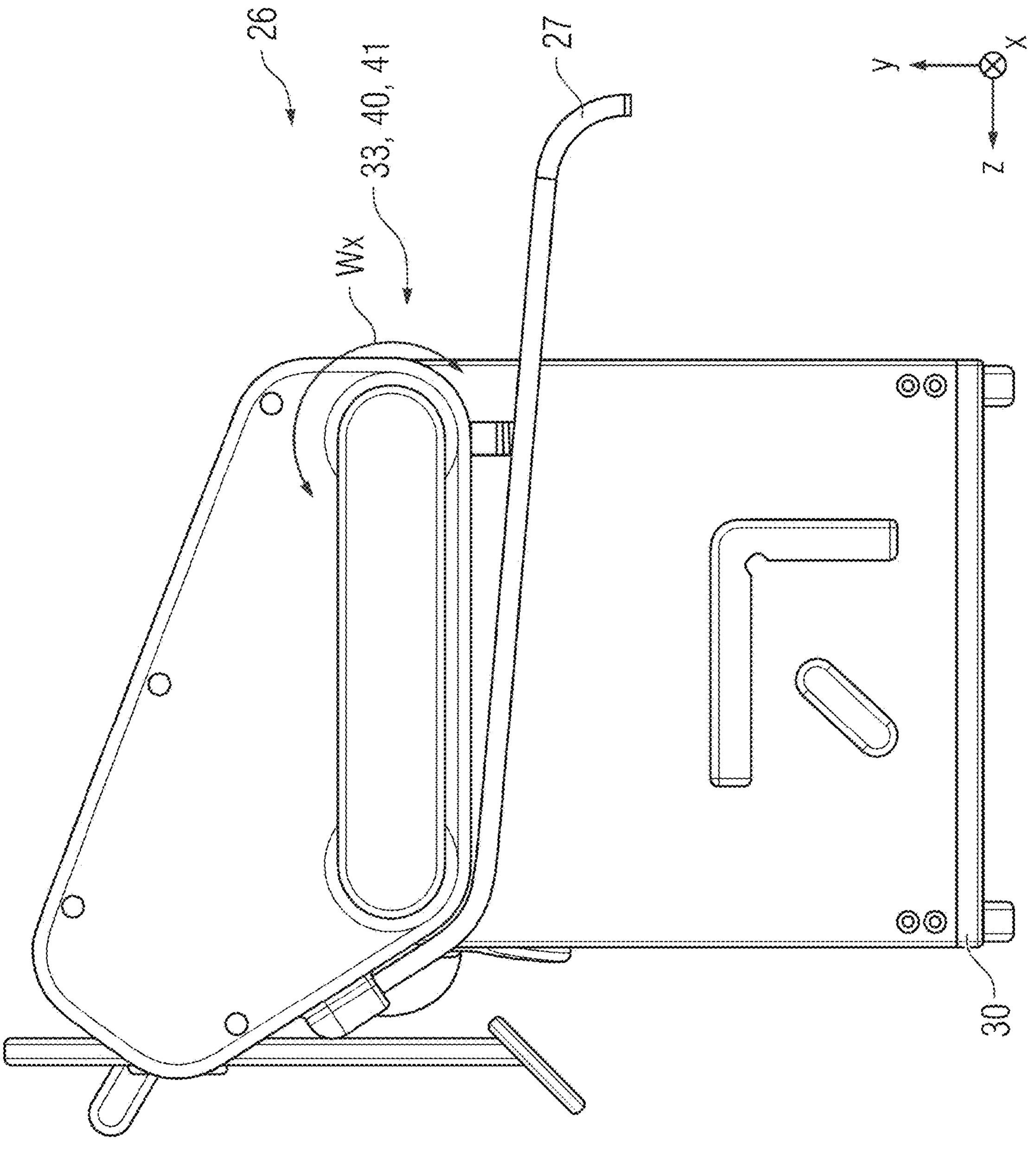
FIG. 6 shows a representation of an aspect of a local coil in accordance with the invention.

FIG. 6 illustrates an aspect of the local coil 26 in accordance with the disclosure in which the holding element 31 and the antenna 32 have been transferred by means of the guide mechanism 40 into a second open position along an arcuate path starting from the open position that is illustrated in FIG. 5. In this case, the arcuate path can be characterized by a movement trajectory of the holding element 31 and/or the antenna 32, which is produced by a rotation of the guide mechanism 40 about the direction of rotation Wx. The guide mechanism can, in particular, be a first guide mechanism in accordance with an aspect described above.

In a preferred aspect of the local coil 26, the guide mechanism 40 and the guide mechanism 41 of the guide system 33 are mechanically coupled or integrated. This can mean that the holding element 31 having the antenna 32 is moved both along the Y direction and along the direction of rotation Wx when the local coil 26 is transferred from the closed position into the open position (or vice versa) by means of the guide mechanisms 40 and 41. It is also conceivable that, during the transfer of the local coil 26 from the closed position into the open position (in reverse), the holding element 31 is first positioned along a movement trajectory that is predefined by the guide mechanism 41 and then along a movement trajectory that is predefined by the guide mechanism 40. In this case, the movement trajectory of the holding element 31 can be characterized by an arcuate path, which essentially corresponds to a section of an elliptical path.

Figure 9:
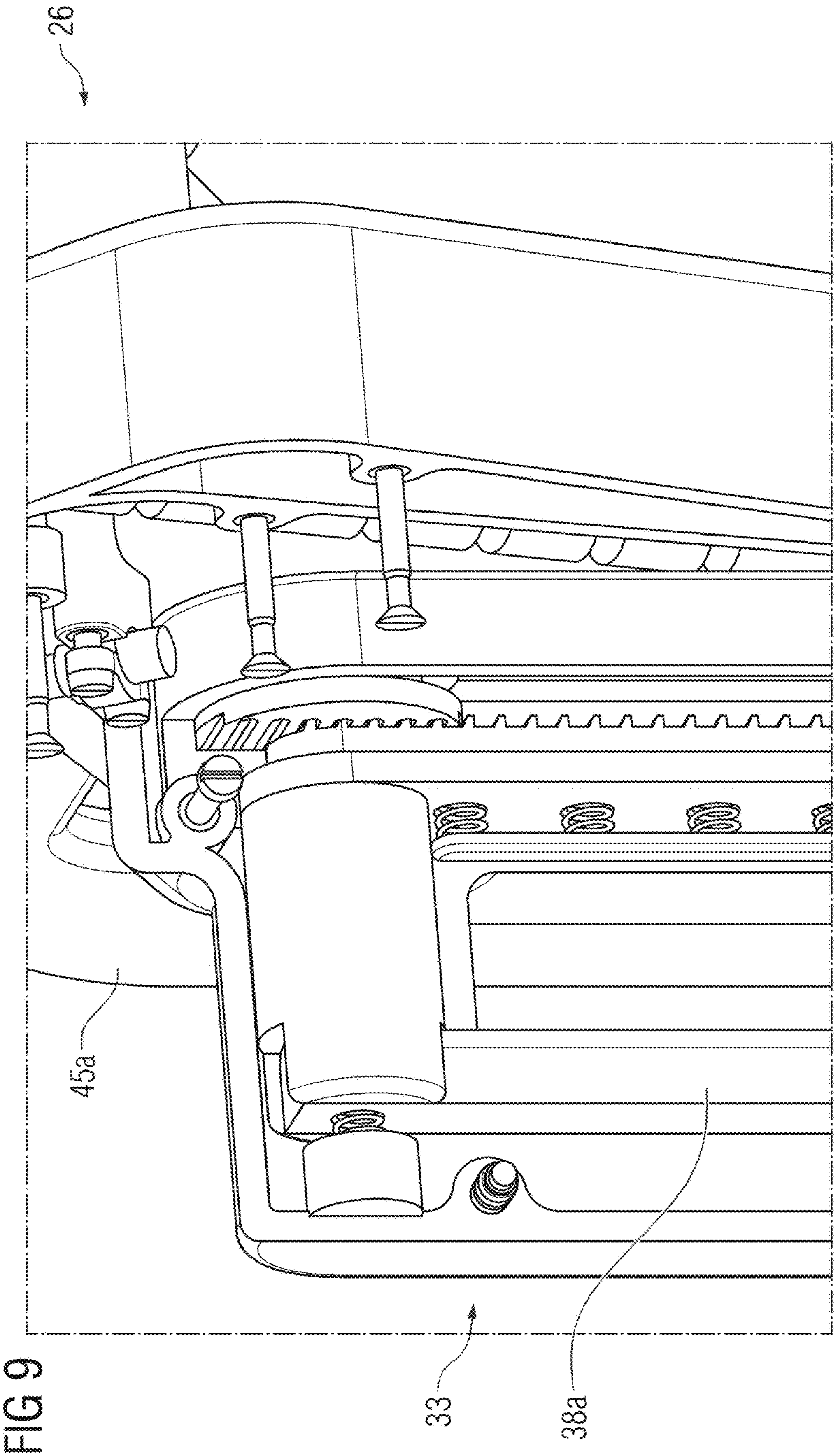
FIG. 9 shows a representation of an aspect of a local coil in accordance with the invention.

FIG. 9 illustrates an aspect in which the local coil 26 in accordance with the disclosure has a locking mechanism 38*a*. The locking mechanism 38*a* is designed in the present case so as to enable positioning of the holding element 31 by means of the guide mechanism 40 or so as to fix the guide mechanism 40 in a desired position. The locking mechanism 38*a* comprises a latching element that is mounted on spring elements, and said latching element can be released from a complementary latching element of the guide system 33, in particular of the guide mechanism 40, by means of the manual application of force by a user. Due to an engagement of the latching element with the complementary latching element of the guide mechanism 40, the guide mechanism 40 and the guide mechanism 41 can be mechanically coupled, as a result of which the holding element 31 can be guided (e.g., along an arcuate path or an elliptical path) when the guide system 33 is actuated along a movement trajectory that results from a superposition of the movement trajectories of the guide mechanisms 40 and 41. In this example, the guide mechanism 40 is released for guiding the holding element 31 in a starting position of the locking mechanism 38*a*. The guide mechanism 40 can be decoupled from the guide mechanism 41 by actuating the locking mechanism 38*a*, so that a movement of the holding element 31 by means of the guide system 33 is limited to a movement trajectory that is defined by the guide mechanism 41 (for example, to a straight line along the Y direction).

In addition to the aspect that is illustrated in FIG. 9, modifications of the configuration of the locking mechanism 38*a* are, of course, conceivable. For example, the locking mechanism 38*a* can be designed so as to release the guide mechanism 40 and/or the guide mechanism 41 of the guide system 33 in dependence upon the application of force by the user. The locking mechanism 38*a* can furthermore have an adaptation element (not illustrated) that is designed so as to variably adjust a mechanical resistance of the guide system 33, in particular of the guide mechanism 40 and/or of the guide mechanism 41.

Although the aspects of the disclosure have been further illustrated and described in detail by the preferred exemplary aspects, the disclosure is nevertheless not limited in this regard by the disclosed examples, and other variations can be derived therefrom by the person skilled in the art without departing from the protective scope of the aspects of the disclosure.

The invention claimed is:

1. A local coil for a magnetic resonance apparatus, comprising:

at least one antenna designed to receive radio frequency signals in a frequency and power range of a magnetic resonance measurement;

a holding element designed to hold the at least one antenna in a position that is appropriate for application on a diagnostically relevant body region of a patient, wherein the at least one antenna is mechanically connected to the holding element;

a base element, wherein a first end of the holding element is mechanically connected to the base element and wherein a second end of the holding element opposite the first end is free-floating;

a guide system that is mechanically connected to the base element and the holding element, and is designed to position the holding element variably with respect to the base element; and a third guide mechanism that is designed to enable rotation of the at least one antenna about an axis of the third guide mechanism, wherein the bolding element bas a cylindrical body, and the third guide mechanism is designed to enable the at least one antenna to rotate about an axis of the cylindrical body of the holding element.

2. The local coil as claimed in claim 1, wherein the guide system has a first guide mechanism that is designed to guide the holding element relative to the base element along an arcuate path.

3. The local coil as claimed in claim 1, wherein the guide system has a second guide mechanism that is designed to variably position the holding element essentially along a surface normal of a support surface that is defined by the base element.

4. The local coil as claimed in claim 1, further comprising:

a locking mechanism that is designed to enable positioning of the holding element using the guide system and/or to fix the guide system in a desired position.

5. The local coil as claimed in claim 4, wherein the locking mechanism has an adaptation element that is designed to variably adjust a mechanical resistance of the guide system.

6. The local coil as claimed in claim 1, further comprising:

a second locking mechanism that is designed to enable the at least one antenna to rotate about the axis of the third guide mechanism and/or to fix the third guide mechanism in a desired position.

7. The local coil as claimed in claim 1, further comprising:

a fourth guide mechanism that is mechanically connected to the holding element and is designed to variably position an auxiliary element along a tangent to a surface of the holding element.

8. The local coil as claimed in claim 1, wherein the base element has first and second delimiting elements that flank a capture region from two opposite sides, the capture region being defined by the base element, wherein a height of the first delimiting element exceeds a height of the second delimiting element.

9. The local coil as claimed in claim 8, wherein the second delimiting element and the holding element are separated from one another by a free space, wherein the free space extends along a surface normal of a support surface that is defined by the base element in a direction of a capture region of the local coil.

10. The local coil as claimed in claim 8, wherein at least one delimiting element comprises a grip element.

11. The local coil as claimed in claim 8, further comprising:

a support element that is connected to the base element in a position that is appropriate for the application, and is designed to stabilize the diagnostically relevant body region that is positioned in a capture region of the local coil in a predetermined position with respect to the local coil.

12. The local coil as claimed in claim 11, wherein the support element has an elastic material, and wherein the first delimiting element and the second delimiting element are designed to hold the support element in a position that is appropriate for the application in the local coil using elastic restoring forces of the elastic material.

13. The local coil as claimed in claim 1, wherein the holding element and/or the base element comprise an electrical interface that is designed to connect the at least one antenna to a receiving unit of a magnetic resonance apparatus.

14. A magnetic resonance apparatus, comprising:

a local coil as claimed in claim 1, wherein the magnetic resonance apparatus is designed to acquire magnetic resonance data of the diagnostically relevant body region of the patient using the local coil.

15. A local coil for a magnetic resonance apparatus, comprising:

at least one antenna designed to receive radio frequency signals in a frequency and power range of a magnetic resonance measurement;

a holding element designed to hold the at least one antenna in a position that is appropriate for application on a diagnostically relevant body region of a patient, wherein the at least one antenna is mechanically connected to the holding element;

a guide mechanism that is mechanically connected to the holding element and is designed to variably position an auxiliary element along a tangent to a surface of the holding element;

a base element, wherein a first end of the holding element is mechanically connected to the base element and wherein a second end of the holding element opposite the first end is free-floating, wherein the base element has first and second delimiting elements that flank a capture region from two opposite sides, the capture region being defined by the base element, wherein a height of the first delimiting element exceeds a height of the second delimiting element, wherein the lower second delimiting element is configured to enlarge a free space or gap between the holding element and a nearest point of the base element; and a guide system that is mechanically connected to the base element and the holding element, and is designed to position the holding element variably with respect to the base element.

* * * * *